United States Patent [19]

Okorley et al.

[11] Patent Number: 4,723,019

[45] Date of Patent: Feb. 2, 1988

[54] POLYCHLOROPYRIDINES FROM POLYCHLOROPICOLINES CONTAMINATED WITH HEXACHLOROBENZENE

[75] Inventors: Jonathan A. Okorley, Pittsburg; Thomas J. Dietsche, Berkeley, both of Calif.

[73] Assignee: The Dow Chemical Company, Midland, Mich.

[21] Appl. No.: 925,331

[22] Filed: Oct. 31, 1986

[51] Int. Cl.$^4$ ............................................ C07D 211/72
[52] U.S. Cl. .................................................... 546/345
[58] Field of Search ........................................ 546/345

[56] References Cited

U.S. PATENT DOCUMENTS

| 3,420,833 | 1/1969 | Taplin | 546/345 |
| 4,256,894 | 3/1981 | Dietsche et al. | 546/345 |
| 4,517,369 | 5/1985 | Marinak et al. | 546/345 |

Primary Examiner—Alan L. Rotman
Assistant Examiner—Robert C. Whittenbaugh

[57] ABSTRACT

Trichloro- and tetrachloro(trichloromethyl)pyridines contaminated with hexachlorobenzene are converted to useful products containing acceptably low levels of hexachlorobenzene by chlorination under conditions of chlorinolysis to tetrachloro- and pentachloropyridine and then removing the hexachlorobenzene by distillation. For example, 2,3,6-trichloro-5-(trichloromethyl)-pyridine contaminated with hexachlorobenzene is converted to 2,3,5,6-tetrachloropyridine containing less than 50 ppm hexachlorobenzene.

8 Claims, No Drawings

POLYCHLOROPYRIDINES FROM POLYCHLOROPICOLINES CONTAMINATED WITH HEXACHLOROBENZENE

BACKGROUND OF THE INVENTION

The present invention relates to a process for enhancing the value of mixtures containing polychloropicolines and hexachlorobenzene.

Hexachlorobenzene is an undesirable contaminant that is generally produced as a by-product in high temperature picoline chlorination processes. The removal of this hexachlorobenzene contaminant from the polychloropyridine and polychloropicoline products obtained in such processes is critical to the usefulness of the products because of the toxicological and environmental properties of this contaminant. Polychloropyridines and polychloropicolines containing substantial amounts of hexachlorobenzene cannot be used directly or as intermediates.

Hexachlorobenzene can be reduced to low levels from mixtures with polychloropyridines and polychloropicolines having boiling points differing from that of hexachlorobenzene by about 40° C. or greater by distillation. Such distillations are usually performed in high efficiency, multiplate stills under reduced pressure. Commercially feasible methods are not available, however, for removing hexachlorobenzene to acceptably low levels from mixtures with more closely boiling polychloropicolines and such mixtures are generally treated as waste. As a result, methods for removing hexachlorobenzene from mixtures with polychloropicolines and recovering usable polychloropyridines would be economically advantageous.

SUMMARY OF THE INVENTION

It has now been found that substantially hexachlorobenzene-free polychloropyridines can be recovered from difficultly separable mixtures containing polychloropicolines and hexachlorobenzene by chlorinating the mixtures, distilling the chlorination product, and recovering polychloropyridines.

In carrying out the process, a mixture comprising essentially a polychloro(trichloromethyl)pyridine of Formula I

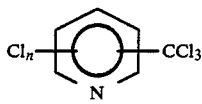

Formula I wherein n is 3 or 4 (which is alternately named a polychloropicoline herein and in chemical practice) and hexachlorobenzene is chlorinated under conditions conducive to chlorinolysis, the resulting chlorination product is distilled to separate the tetrachloropyridine and pentachloropyridine so produced as distillate; and the distilled tetrachloropyridines and pentachloropyridine are recovered, substantially free of hexachlorobenzene.

The 2,3,5,6-, 2,3,4,5-, and 2,3,4,6-tetrachloropyridines and pentachloropyridine obtained in the present process are useful as intermediates for the production of insecticides and herbicides. 2,3,5,6-Tetrachloropyridine and pentachloropyridine are especially valuable intermediates.

The hexachlorobenzene is generally left in the undistilled residue of the distillation and is generally discarded as waste along with any inseparable polychloropicolines remaining and any tars.

The polychloro(trichloromethyl)pyridine mixtures with hexachlorobenzene subjected to the present process typically contain other polychloropyridines and polychloropicolines in addition to one or more polychloro(trichloromethyl)pyridines of Formula I.

This invention takes advantage of the surprising circumstances of compounds of Formula I wherein chlorination leads to products having lower boiling points.

DETAILED DESCRIPTION OF THE INVENTION

The chlorination of picolines under conditions designed to produce valuable polychloropicolines and/or polychloropyridines generally produces mixtures containing some polychloropicolines of Formula I along with some hexachlorobenzene. Because of this, process streams containing polychloropicolines of Formula I and hexachlorobenzene are typically encountered in such processes in commercial practice. These mixtures are generally discarded as waste. Mixtures containing polychloropicolines of Formula I and hexachlorobenzene produced by the chlorination of picolines or in other ways are the feed stock of the present invention. They are distinguished by the fact that hexachlorobenzene cannot be removed from them to acceptably low levels by distillation in commercially feasible stills because the boiling points of the polychloropicolines of Formula I (about 300° C. to about 350° C.) are too close to the boiling point of hexachlorobenzene (323°–326° C.).

Polychloropyridines of Formula I include, for example, tetrachloro-2-(trichloromethyl)pyridine, 2,3,5-trichloro-6-(trichloromethyl)pyridine, 2,3,4-trichloro-6-(trichloromethyl)pyridine, 2,4,5-trichloro-6-(trichloromethyl)pyridine, 3,4,5-trichloro-6-(trichloromethyl)pyridine, 2,3,6-trichloro-5-(trichloromethyl)pyridine, 2,3,4-trichloro-5-(trichloromethyl)pyridine, and 2,3,6-trichloro-4-(trichloromethyl)pyridine. Preferred compounds of Formula I include 2,3,5-trichloro-6-(trichloromethyl)pyridine and 2,3,6-trichloro-5-(trichloromethyl)pyridine.

The chlorination step of the process can be carried out in the liquid or the vapor phase in the presence or absence of catalysts or u.v. light. The conditions, however, must be such as to cause chlorinolysis of the trichloromethyl moiety which effectively converts a polychloropicoline to a polychloropyridine. Suitable reaction conditions are taught in U.S. Pat. No. 3,420,833 for vapor phase operations and in U.S. Pat. Nos. 4,256,894, 4,517,369, and application Ser. No. 648,109, filed Sept. 7, 1984 for liquid phase operations. The teachings of each of these prior art citations is hereby incorporated into the present specification by reference. In general, chlorination temperatures of about 500° C. and retention times of about 5 to 100 seconds are required for vapor phase operations and chlorination temperatures of at least 170° C. and reaction times of about 1 to 20 days are required for liquid phase operations. Temperatures above 200° C. are generally employed in the latter case and ferric chloride is commonly employed as a catalyst.

The products of the chlorination step are 2,3,5,6-, 2,3,4,5-, and 2,3,4,6-tetrachloropyridine and pentachloropyridine. These polychloropyridines have boiling points of about 252°, 251°, 250°, and 281° C., respectively, and are separable from hexachlorobenzene by distillation. Processes in which the product obtained is 2,3,5,6-tetrachloropyridine or pentachloropyridine are preferred.

The distillation step of the process can be carried out in any multiplate distillation apparatus capable of making the required separations. Suitability of an apparatus for the separation and suitable operating parameters for any appropriate apparatus can be estimated by well known techniques based on the difference in boiling points involved and the maximum amount of hexachlorobenzene to be allowed in the product. The distillation is often conducted under reduced pressure to allow operation at a lower temperature.

The distillation is conducted so that the desired tetra- and/or pentachloropyridines are separated as distillate. This distillate is substantially free of hexachlorobenzene. It can be further purified to still lower levels of hexachlorobenzene by further distillation if required or desired.

The hexachlorobenzene can be left in the distillation residue along with any tars or can be separated from the tars as a distillate. In either case, it is normally a waste product and is discarded, typically by incineration.

Depending on the polychloropicolines employed, the chlorination conditions, and the distillation parameters, the substantially hexachlorobenzene free polychloropyridine obtained may be a single polychloropyridine of high purity or a mixture of polychloropyridines. In the former case it can be used directly as an intermediate; in the latter case it is typically further distilled or otherwise purified, such as by crystal refining or solvent recrystallization, before use.

The 2,3,5,6-, 2,3,4,5-, or 2,3,4,6-tetrachloropyridine or pentachloropyridine or mixtures thereof produced in the distillation are recovered and held for future use or fed directly to other processes. These products are substantially free of hexachlorobenzene and are, therefore, useful as intermediates in the production of agricultural pesticides. They generally contain less than 1000 ppm (0.1 percent) hexachlorobenzene. Products containing less than 200 ppm (0.02 percent) are preferred and those containing less than 50 ppm (0.005 percent) are more preferred.

The following example is presented to illustrate the invention and should not be construed as limiting the scope: A mixture of polychloropicolines and polychloropyridines containing hexachlorobenzene (1232 g) in a 2 liter 3 necked flask was chlorinated at 200° C. in the liquid phase with stirring in the presence of 2.0 g (0.16 percent) of ferric chloride with a chlorine flow of 8 g per hour for 12 days. The initial and final analysis (gas-liquid chromatography/mass spectometry) were as follows:

| Constituent | Initial, % | Final, % |
| --- | --- | --- |
| 2,3-dichloro-5-(trichloromethyl)pyridine | 2.6* | 1.0* |
| 2,6-dichloro-5-(trichloromethyl)pyridine | 5.3 | 0.0 |
| 3,6-dichloro-5-(trichloromethyl)pyridine | 0.9 | 0.2 |
| 2,3,6-dichloro-5-(trichloromethyl)pyridine | 63.5 | 18.3 |
| tetrachloro-5-(trichloromethyl)pyridine | 0.4 | 0.5 |
| hexachlorobenzene | 15.5 | 18.5 |
| pentachloropyridine | 10.7 | 25.1 |
| 2,3,5,6-tetrachloropyridine | 0.0 | 32.5 |
| unknowns | 1.1 | 3.9 |

*includes some unknowns

The product mixture obtained in the example is distillable into fractions consisting essentially of pentachloropyridine containing less than 200 ppm hexachlorobenzene and 2,3,5,6-tetrachloropyridine containing less than 50 ppm hexachlorobenzene.

What is claimed is:

1. A process for removing hexachlorobenzene from a mixture comprising essentially a polychloropicoline of the formula

wherein n is 3 or 4 and hexachlorobenzene which process comprises chlorinating the mixture under conditions condusive to chlorinolysis to obtain a chlorination product; distilling the chlorination product to separate the tetrachloropyridines and pentachloropyridine contained therein as distillate, substantially free of hexachlorobenzene, and the hexachlorobenzene contained therein as undistilled residue; and recovering the distillate.

2. A process according to claim 1 wherein a liquid phase chlorination optionally employing ferric chloride as a catalyst is employed.

3. A process according to claim 1 wherein the polychloropicoline is 2,3,5-trichloro-6-(trichloromethyl)-pyridine.

4. A process according to claim 1 wherein the polychloropicoline is 2,3,6-trichloro-5-(trichloromethyl)-pyridine.

5. A process according to claim 1 wherein the recovered tetrachloropyridine is 2,3,5,6-tetrachloropyridine.

6. A process according to claim 1 wherein pentachloropyridine is recovered.

7. A process according to claim 1 wherein the recovered tetrachloropyridine or pentachloropyridine contains less than 1000 ppm hexachlorobenzene.

8. A process according to claim 1 wherein the mixture comprising a polychloropicoline and hexachlorobenzene contains other polychloropicolines and polychloropyridines.

* * * * *